(12) United States Patent
Bezencon et al.

(10) Patent No.: US 7,915,259 B2
(45) Date of Patent: Mar. 29, 2011

(54) DIAZABICYCLONONENE DERIVATIVES AND USE THEREOF

(75) Inventors: Olivier Bezencon, Riehen (CH); Daniel Bur, Therwil (CH); Walter Fischli, Allschwil (CH); Lubos Remen, Allschwil (CH); Sylvia Richard-Bildstein, Dietwiller (FR); Thierry Sifferlen, Guewenheim (FR); Thomas Weller, Binningen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 322 days.

(21) Appl. No.: 11/795,850

(22) PCT Filed: Jan. 26, 2006

(86) PCT No.: PCT/IB2006/050285
§ 371 (c)(1),
(2), (4) Date: Jul. 23, 2007

(87) PCT Pub. No.: WO2006/079988
PCT Pub. Date: Aug. 3, 2006

(65) Prior Publication Data
US 2008/0161313 A1 Jul. 3, 2008

(30) Foreign Application Priority Data

Jan. 28, 2005 (WO) ............... PCT/EP2005/000842

(51) Int. Cl.
*A61K 31/495* (2006.01)
(52) U.S. Cl. ........................ 514/249; 544/349
(58) Field of Classification Search .............. 544/349
See application file for complete search history.

(56) References Cited

U.S. PATENT DOCUMENTS

| | | | |
|---|---|---|---|
| 6,051,712 | A | 4/2000 | Binggeli et al. |
| 6,150,526 | A | 11/2000 | Binggeli et al. |
| 2005/0176700 | A1 | 8/2005 | Bezencon |
| 2006/0217371 | A1 | 9/2006 | Bezencon |
| 2006/0223795 | A1 | 10/2006 | Bezencon |

FOREIGN PATENT DOCUMENTS

| | | |
|---|---|---|
| WO | WO03/093267 | 11/2003 |
| WO | WO2004/096116 | 11/2004 |
| WO | WO2004/096804 | 11/2004 |
| WO | WO2004/105762 | 12/2004 |

OTHER PUBLICATIONS

West, Anthony R., Solid State Chemistry and its Applications, Wiley, New York, 1988, pp. 358 and 365.*
U.S. Appl. No. 11/915,594, filed Sep. 4, 2008, Bezencon, et al.
Waeber B. et al., "The renin-angiotensin system: role in experimental and human hypertension", Handbook of Hypertension, vol. 8, 1986, pp. 489-519.

*Primary Examiner* — James O Wilson
*Assistant Examiner* — Brian McDowell
(74) *Attorney, Agent, or Firm* — Hoxie & Associates LLC

(57) ABSTRACT

The invention relates to a novel 3,9-diazabicyclo[3.3.1]nonene derivative of formula (I), enantiomers thereof, and their use thereof as active ingredients in the preparation of pharmaceutical compositions. The invention also concerns related aspects including processes for the preparation of the compounds, pharmaceutical compositions containing at least one compound of formula (I):

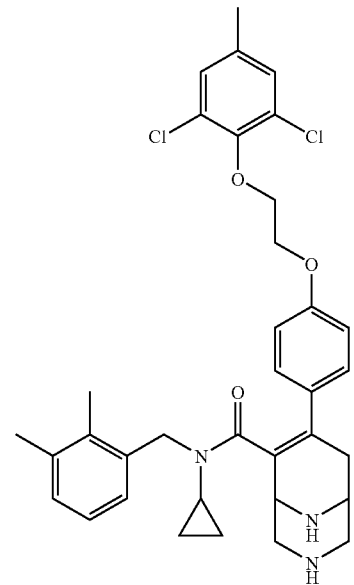

(I)

or (I'):

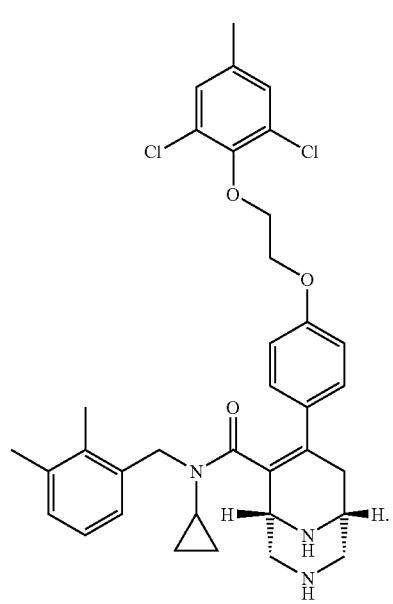

(I')

and especially their use as inhibitors of renin.

2 Claims, No Drawings

OTHER PUBLICATIONS

Weber M. A., "Clinical Experience With the Angiotensin II Receptor Antagonist Losartan", Am. J. Hypertens., 1992, 5, pp. 247s-251s.

Rosenberg M. E. et al., "The paradox of the renin-angiotensin system in chronic renal disease", Kidney International, 1994, vol. 45, pp. 403-410.

Breyer J. A. et al., "Angiotensin converting enzyme inhibition in diabetic nephropathy", Kidney International, 1994, vol. 45, pp. S156-S160.

Vaughan D. E. et al., "Angiotensin converting enzyme inhibitors and cardiovascular remodelling", Cardiovasc. Res., 1994, vol. 28, pp. 159-165.

Fouad-Tarazi F. et al., "The Renin-Angiotensin System and Treatment of Heart Failure", Am. J. Med., 1988, vol. 84 (Suppl. 3A), pp. 83-86.

Pfeffer M A et al, "Effect of captopril on mortality and morbidity in patients with left ventricular dysfunction after myocardial inraction" N. Engl. J. Med., 1992, pp. 669-677.

Kleinert H. D., "Renin Inhibition", Cardiovasc. Drugs and Therapy, 1995, vol. 9, pp. 645-655. Husain A., "The chymase-angiotensin system in humans" J. Hypertens., 1993, vol. I I, pp. 1155-1159.

Israili Z. H. et al., "Cough and angioneurotic edema associated with angiotensin-converting enzyme inhibitor therapy" Annals of Internal Medicine, 1992, vol. 117, pp. 234-242.

Azizi M. et al., "Blood pressure effects of acute intravenous renin or oral angiotensin converting enzyme inhibition in essential hypertension" J. Hypertens.,1994,12, 419-427.

Neutel J M et al, "Immediate blood pressure effects of the renin inhibitor enalkiren and the angiotensin-converting enzyme inhibitor enalaprilat" Am. Heart,1991, 1094-1100.

Rahuel J. etal., "Structure-based drug design: the discovery of novel nonpeptide orally active inhibitors of human renin", Chem. Biol., 2000, vol. 7, pp. 493-504.

Mealy N. E., "Aliskiren Fumarate", Drugs of the Future, 2001, vol. 26, pp. 1139-1148.

Oefner C. et al., "Renin inhibition by substituted piperidines: a novel paradigm for the inhibition of monomeric aspartic proteinases?", Chem. Biol., 1999, vol. 6, pp. 127-131.

Marki H. P. et al., "Piperidine renin inhibitors: from leads to drug candidates", IL Farmaco, 2001, vol. 56, pp. 21-27.

Gould, Philip, "Salt selection for basic drugs", International Journal of Pharmaceutics, 1986, vol. 33, pp. 201-217.

Mark Gibson, Editor, Pharmaceutical Preformulation and Formulation, IHS Health Group, Englewood, Co, USA, 2001.

Majewski M. et al., "Synthesis of Tropane Alkaloids via enantioselective deprotonation of tropinone", J. Org. Chem., 1995, vol. 60, pp. 5825-5830.

Fischli W, etal., "Ro 42-5892 is a potent orally active renin inhibitor in primates", Hypertension, 1991, vol. 18, pp. 22-31.

* cited by examiner

DIAZABICYCLONONENE DERIVATIVES AND USE THEREOF

CROSS REFERENCE TO RELATED APPLICATIONS

This application is a U.S. filing under 35 U.S.C. 371 of PCT/IB06/50285, filed on Jan. 26, 2006, which claims the benefit of PCT/EP2005/000842, filed on Jan. 28, 2005, the disclosures of each of which are incorporated herein by reference. The invention relates to novel compounds of the formula (I) and the enantiomer thereof of formula (I'). The invention also concerns related aspects including processes for the preparation of the compounds, pharmaceutical compositions containing at least one compound of formula (I) or (I') and especially their use as renin inhibitors in cardiovascular events and renal insufficiency.

BACKGROUND

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Birkenhager W. H., Reid J. L. (eds): *Hypertension*, Amsterdam, Elsevier Science Publishing Co, 1986, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N. Engl. J. Med.*, 1992, 327, 669).

The rationale to develop renin inhibitors is the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.*, 1993, 11, 1155). In patients inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the $AT_1$ receptor (e.g. by losartan) on the other hand overexposes other AT-receptor subtypes (e.g. $AT_2$) to Ang II, whose concentration is significantly increased by the blockade of $AT_1$ receptors. In summary, renin inhibitors are expected to demonstrate a different pharmaceutical profile than ACE inhibitors and $AT_1$ blockers with regard to efficacy in blocking the RAS and in safety aspects.

Only limited clinical experience (Azizi M. et al., *J. Hypertens.*, 1994, 12, 419; Neutel J. M. et al., *Am. Heart*, 1991, 122, 1094) has been created with renin inhibitors because of their insufficient oral activity due to their peptidomimetic character (Kleinert H. D., *Cardiovasc. Drugs*, 1995, 9, 645). The clinical development of several compounds has been stopped because of this problem together with the high cost of goods. Only one compound containing four chiral centers has entered clinical trials (Rahuel J. et al., *Chem. Biol.*, 2000, 7, 493; Mealy N. E., *Drugs of the Future*, 2001, 26, 1139). Thus, renin inhibitors with good oral bioavailability and long duration of action are required. Recently, the first non-peptide renin inhibitors were described which show high in vitro activity (Oefner C. et al., *Chem. Biol.*, 1999, 6, 127; Patent Application WO 97/09311; Märki H. P. et al., *Il Farmaco*, 2001, 56, 21). However, the development status of these compounds is not known.

The present invention relates to renin inhibitors of a non-peptidic nature and of low molecular weight. Described are orally active renin inhibitors of formula (I) and (I') which have a long duration of action and which are active in indications beyond blood pressure regulation where the tissular renin-chymase system may be activated leading to pathophysiologically altered local functions such as renal, cardiac and vascular remodeling, atherosclerosis, and possibly restenosis.

SUMMARY OF THE INVENTION

In particular, the present invention relates to a novel compound of the structural formula (I): (1R*,5S*)-7-{4-[2-(2,6-dichloro-4-methylphenoxy)ethoxy]phenyl}-3,9-diazabicyclo[3.3.1]non-6-ene-6-carboxylic acid cyclopropyl-(2,3-dimethylbenzyl)amide;

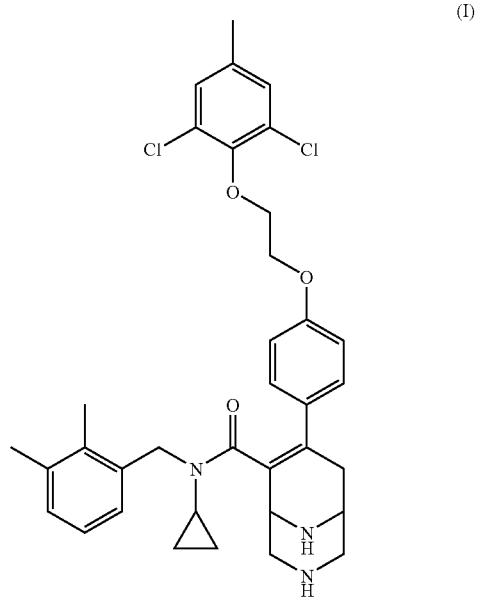

(I)

and optically pure enantiomers or a mixture of enantiomers such as a racemate; as well as pharmaceutically acceptable salts, solvent complexes and morphological forms thereof.

A preferred enantiomer is the one represented by formula (I'): (1R,5S)-7-{4-[2-(2,6-dichloro-4-methylphenoxy) ethoxy]phenyl}-3,9-diazabicyclo[3.3.1]non-6-ene-6-carboxylic acid cyclopropyl-(2,3-dimethylbenzyl)amide;

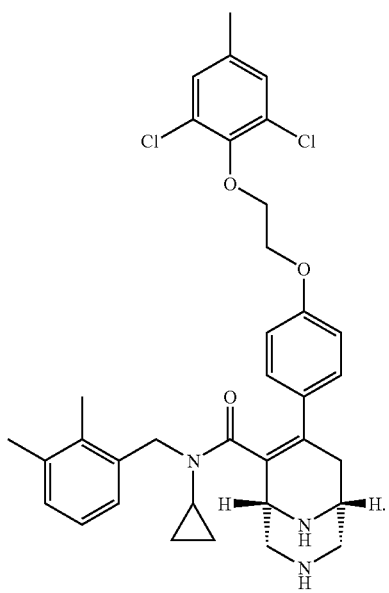

(I')

Where, within this disclosure, the plural form is used for compounds, salts, pharmaceutical compositions, diseases and the like, this is intended to mean also a single compound, salt, or the like.

Any reference to a compound of formula (I) is to be understood as referring also to the optically pure enantiomers, or a mixture of enantiomers such as a racemate, as well as salts (especially pharmaceutically acceptable salts) and solvent complexes (including hydrates) of such compounds, and morphological forms, as appropriate and expedient, whereas any reference to a compound of formula (I') is to be understood as referring also to salts (especially pharmaceutically acceptable salts) and solvent complexes (including hydrates) of such compound, and morphological forms, as appropriate and expedient.

DETAILED DESCRIPTION

The expression pharmaceutically acceptable salts encompasses either salts with inorganic acids or organic acids like hydrochloric acid, hydrobromic acid, hydroiodic acid, sulfuric acid, phosphoric acid, nitric acid, citric acid, formic acid, acetic acid, maleic acid, tartaric acid, fumaric acid, benzoic acid, palmoic acid, stearic acid, methanesulfonic acid, p-toluenesulfonic acid, and the like that are non toxic to living organisms. The bis-methanesulfonic acid salt is especially preferred. For other examples of pharmaceutically acceptable salts, reference can be made to "Salt selection for basic drugs", Int. J. Pharm. (1986), 33, 201-217.

The compounds of the formula (I) contain two inter-dependent asymmetric carbon atoms having the relative stereochemistry (1R*,5S*) and may be prepared in form of the optically pure enantiomers (1R,5S)-7-{4-[2-(2,6-dichloro-4-methylphenoxy)ethoxy]phenyl}-3,9-diazabicyclo[3.3.1] non-6-ene-6-carboxylic acid cyclopropyl-(2,3-dimethylbenzyl)amide (i.e. compound of formula (I') which is preferred) and (1S,5R)-7-{4-[2-(2,6-dichloro-4-methylphenoxy) ethoxy]phenyl}-3,9-diazabicyclo[3.3.1]non-6-ene-6-carboxylic acid cyclopropyl-(2,3-dimethylbenzyl)amide, or as a mixture of the two enantiomers such as a racemate. The present invention encompasses all these forms. Mixtures may be separated in a manner known per se, i.e. by column chromatography, thin layer chromatography, HPLC, or crystallization. A resolution of the racemate on the final compound or any chemical intermediate is possible as well, using an enantiomerically pure substance bearing an acidic moiety. For instance such a resolution is possible using tartaric acid with compound 1 in Scheme 1.

The compounds of formula (I) and (I') are useful for the treatment and/or prophylaxis of diseases associated with a dysregulation of the renin-angiotensin system, in particular diseases such as or related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases related to the renin-angiotensin system.

The compounds of formula (I) and (I') are especially useful for the treatment and/or prophylaxis of hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment or prophylaxis of diseases, which are associated with a dysregulation of the renin-angiotensin system, in particular to a method for the treatment or prophylaxis of the above-mentioned diseases, said methods comprising administering to a human being or animal a pharmaceutically active amount of a compound of formula (I) or (I').

A further aspect of the present invention relates to pharmaceutical compositions comprising a compound of formula (I) or (I') and a pharmaceutically acceptable carrier material. These pharmaceutical compositions may be used for the treatment and/or prophylaxis of the above-mentioned diseases. The pharmaceutical compositions can be used for enteral, parenteral, or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The invention also relates to the use of a compound of formula (I) or (I') for the preparation of pharmaceutical compositions for the treatment and/or prophylaxis of the above-mentioned diseases.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of formula (I) or (I') or their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injections are, for example, water, alcohols, polyols, glycerols and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of compounds of formula (I) and (I') can vary within wide limits depending on the disease to be controlled, the age and the individual condition of the patient and the mode of administration, and will, of course, be fitted to the individual requirements in each particular case.

In a preferred embodiment, this amount is comprised between 2 mg and 1000 mg per day.

In a particularly preferred embodiment, this amount is comprised between 1 mg and 500 mg per day.

In a more particularly preferred embodiment, this amount is comprised between 5 mg and 200 mg per day.

Another aspect of the invention is related to a process for the preparation of a pharmaceutical composition comprising a compound of formula (I) or (I'). According to said process, one or two active ingredients of formula (I) and (I') are mixed with inert excipients in a manner known per se.

Compounds of formula (I) and (I') or the above-mentioned pharmaceutical compositions are also of use in combination with other pharmacologically active compounds such as ACE-inhibitors, neutral endopeptidase inhibitors, angiotensin II receptor antagonists, endothelin receptors antagonists, vasodilators, calcium antagonists, potassium activators, diuretics, sympatholytics, beta-adrenergic antagonists, alpha-adrenergic antagonists, and/or other drugs beneficial for the prevention or the treatment of the above-mentioned diseases such as aldosterone antagonists, 11beta-hydroxysteroid dehydrogenase type 1 inhibitors and soluble guanylate cyclase activators.

The present invention also relates to pro-drugs of a compound of formula (I) or (I') that convert in vivo to the compound of formula (I) or (I') as such. Any reference to a compound of formula (I) or (I') is therefore to be understood as referring also to the corresponding pro-drugs of the compound of formula (I) or (I'), as appropriate and expedient.

The compounds of the formula (I) and (I') can be manufactured by the methods outlined below, by the method described in the example or by analogous methods.

The synthesis of the compounds of formula (I) and (I') described hereby is one possible synthesis among many other alternatives. Other synthetic routes and methodologies will be apparent to the skilled person in the art.

The bicyclononane derivative 1 (Scheme 1) can be prepared as racemate as described earlier (WO 2003/093267). Preparation of the vinylic triflate 2 proceeds using sodium hydride and N-phenyl-bis(trifluoromethanesulfonimide). A Negishi-coupling between the bicyclic system 2 and the bromophenyl derivative 6 leads to diazabicyclonene 3. Bromophenyl derivative 6 is prepared in three steps from 4-bromophenol, via an alkylation with 2-bromoethanol (→compound 4), then a conversion of the hydroxyl group into an iodine (→compound 5), and finally an aryl ether formation to compound 6. Bicyclononene 3 is then transprotected to bicyclononene 7. Saponification of the ethyl ester under strongly basic conditions leads to a mixture of the carboxylic acid derivatives 8 and 9.

Scheme 1

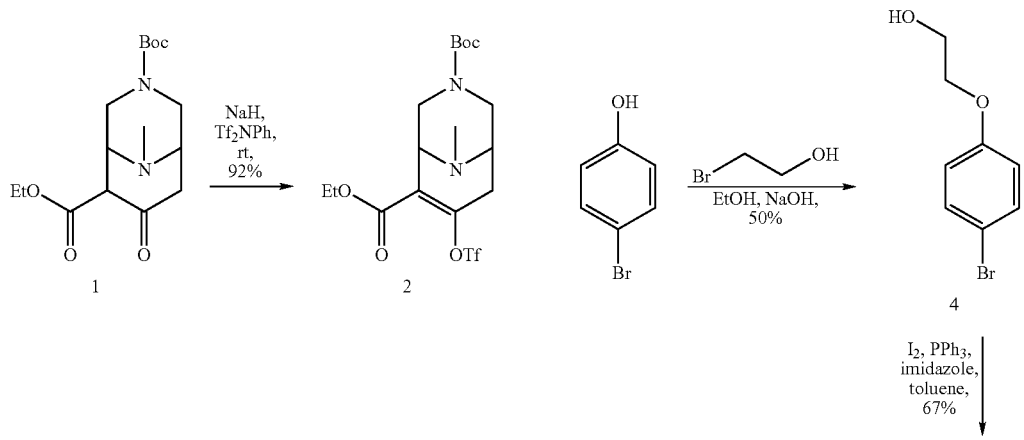

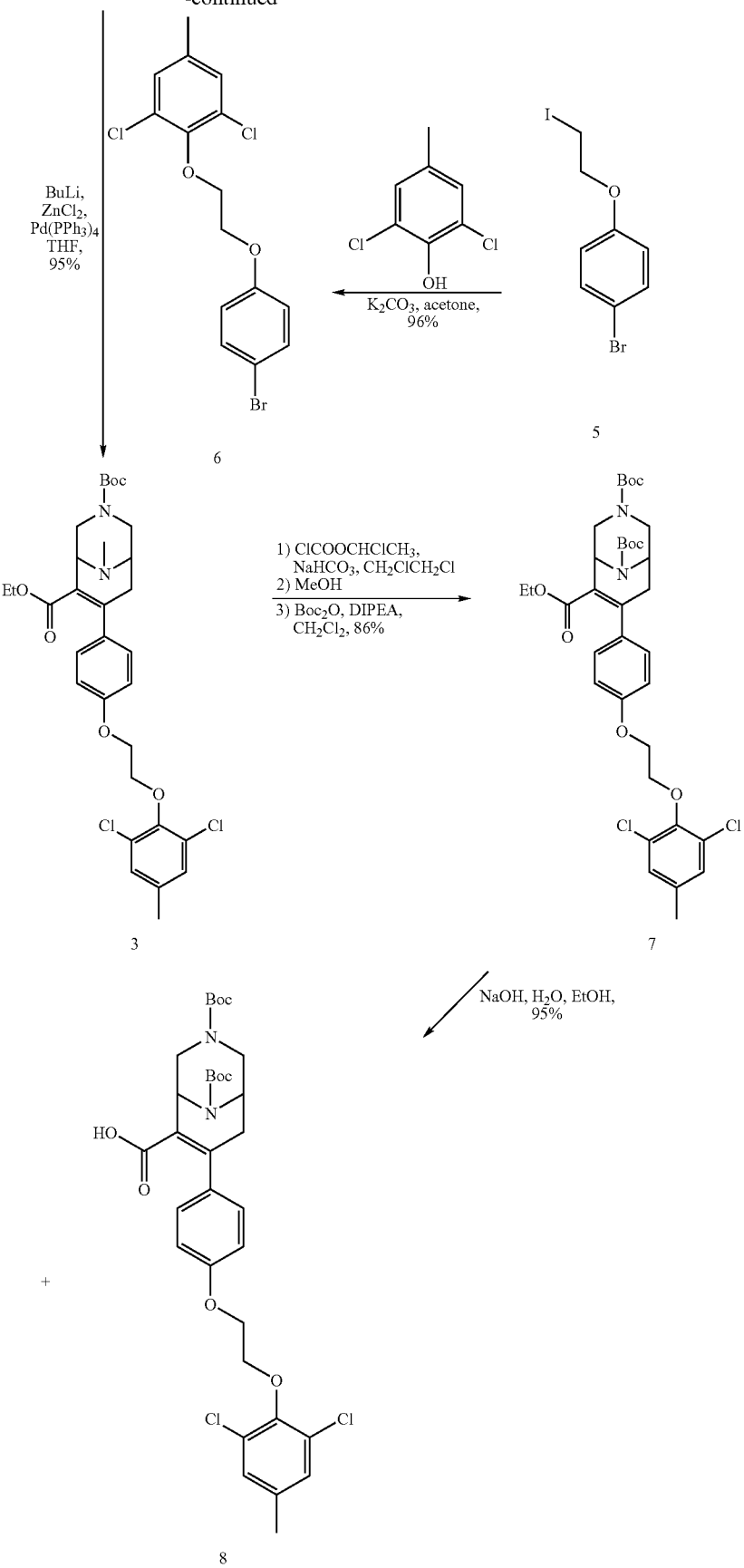

The mixture of compounds 8 and 9 is not separated and used directly further in the amide coupling step with amine derivative 11, which is prepared in one step using a reductive amination (Scheme 2). Amide coupling product 10 is obtained. Cleavage of both Boc-protecting groups leads to compound of general formula (I).
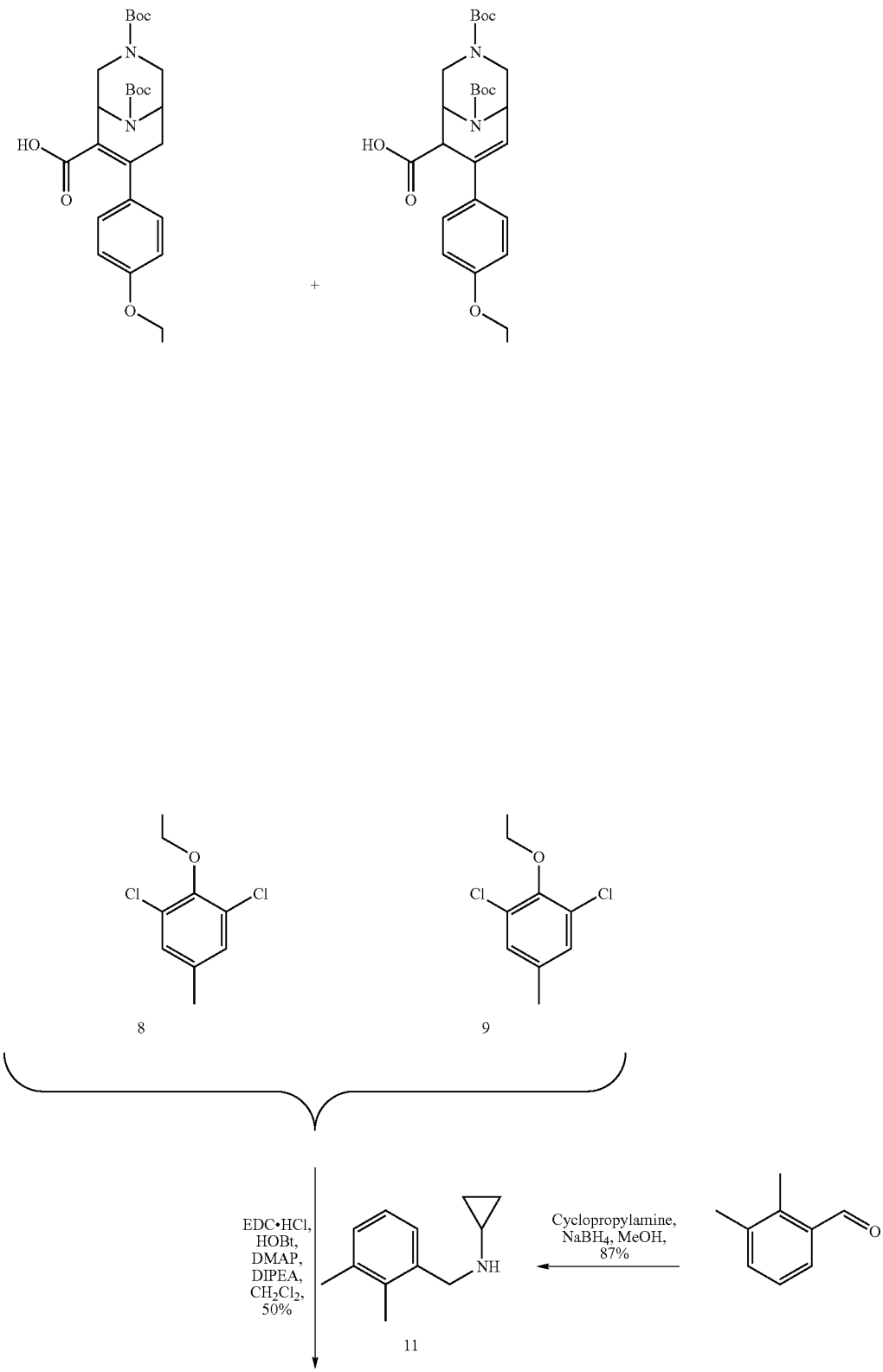
Scheme 2

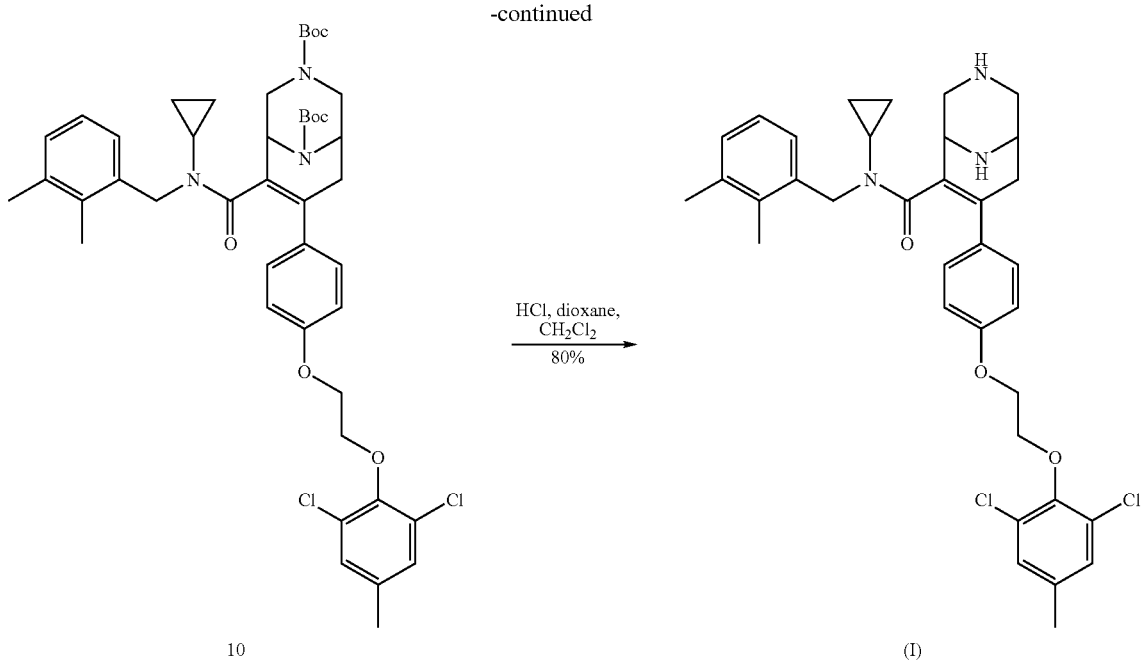

Enantioselective Synthesis

The compounds of the present invention contain two chiral centers which, however, are not independent from each other. The synthetic methods presented so far lead to a racemate. The racemate can be separated into the compound of formula (I') and its enantiomer using a chiral HPLC-column. Also, both enantiomers might be prepared selectively starting from a meso-bicyclononane derivative, like compound 12 (Scheme 3), using an enantioselective acylation (Majewski M., Lasny R., *J. Org. Chem.*, 1995, 60, 5825), as described in WO 2003/093267. Another alternative would be a resolution of the racemate using a chiral, organic acid derivative.

Scheme 3

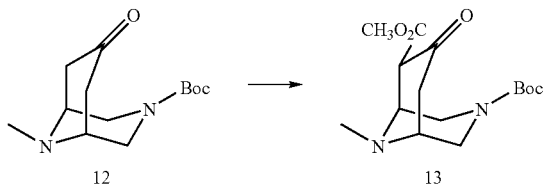

The following example serves to illustrate the present invention in more detail. It is, however, not intended to limit its scope in any manner.

Example

General Remarks

The compound is characterized at least by LC-MS and $^1$H-NMR. Only the LC-MS data are given here (Zorbax SB-AQ column, 5 µm, 4.6×50 mm; eluent A: 0.04% trifluoroacetic acid in water; eluent B: acetonitrile; gradient 5%→100% eluent B over 1.5 min, flow 1 mL/min)

Abbreviations (As Used Herein)
ACE Angiotensin Converting Enzyme
Ang Angiotensin
aq. aqueous
Boc tert-Butyloxycarbonyl
BSA Bovine serum albumine
BuLi n-Butyllithium
DIPEA Diisopropylethylamine
DMAP 4-N,N-Dimethylaminopyridine
DMSO Dimethylsulfoxide
EDC.HCl   Ethyl-N,N-dimethylaminopropylcarbodiimide hydrochloride
EIA Enzyme immunoassay
ES+ Electrospray, positive ionization
Et Ethyl
EtOAc Ethyl acetate
EtOH Ethanol
FC Flash Chromatography
h hour(s)
HOBt Hydroxybenzotriazol
HPLC High Performance Liquid Chromatography
LC-MS liquid chromatography-mass spectrometry
min minute(s)
MeOH Methanol
org. organic
Ph Phenyl
$R_f$ Retention Index (in TLC)
rt room temperature
sat. saturated
sol. Solution
Tf Trifluoromethylsulfonyl
THF Tetrahydrofuran TLC Thin Layer Chromatography
$t_R$ retention time (rac.)-(1R*,5S*)-9-Methyl-7-trifluoromethanesulfonyloxy-3,9-diazabicyclo-[3.3.1]non-6-ene-3,6-dicarboxylic acid 3-tert-butyl ester 6-ethyl ester (2)

Compound 1 (WO 2003/093267, 99.58 g, 305 mmol) was dissolved in dry THF (1450 mL) under a nitrogen atmosphere and the mixture was cooled to 0° C. NaH (16.64 g; 55% dispersion in mineral oil, 381 mmol) was added by portions of 2 g over a period of 35 min, keeping the temperature between 0 and 4° C. A gas evolution was observed. After the addition the reaction mixture was stirred for 75 min at 0 to 4° C. Tf$_2$NPh (128.6 g, 360 mmol) was then added as a solid within 5 min. The reaction mixture became brown. The cooling bath was removed and the reaction was stirred over the weekend at rt. The reaction mixture was poured onto 1 L of ice/water and the THF was removed under reduced pressure. The remaining water phase was extracted with EtOAc (3×500 mL). The combined org. layers were washed with water (500 mL) and brine (500 mL). The org. phase was then dried over MgSO$_4$, filtered, and the solvents were evaporated under reduced pressure. To the crude brown residue (174 g) was added 50 mL of pentane and the mixture was stirred at 4° C. overnight. The precipitate was filtered off and washed with cold hexane (70 mL) and a cold mixture of hexane/diethylether (4:1, 100 mL). This resulted in 84 g of product containing some TfNHPh. This material was filtered over silicagel (75 g). TfNHPh was washed out with heptane. The title product was subsequently washed out with EtOAc (3 times 1 L) to give after evaporation under reduced pressure the title product in three fractions: a) 44.45 g of off white crystals, b) 27.98 g of little brown crystals, and c) 15 g of a yellow oil containing the product and TfNHPh. After 2 days the TfNHPh contained in fractions c) had crystallised. It was filtered to yield 9.43 g of the product as a brown oil.

Treatment of the Mother Liquors

The combined mother liquors obtained above were concentrated under vacuo. The brown oil residue (75 g) was purified by FC (1500 g silica gel) using a gradient of (EtOAc/heptane 1-9→EtOAc). The column was then washed with EtOAc/MeOH 9:1. The title compound was isolated as 25.44 g of an off-white solid as the pure product. LC-MS: $t_R$=0.87 min; ES+: 459.24.

(rac.)-(1R*,5S*)-7-{4-[2-(2,6-Dichloro-4-methylphenoxy)ethoxy]phenyl}-9-methyl-3,9-diazabicyclo[3.3.1]non-6-ene-3,6-dicarboxylic acid 3-tert-butyl ester6-ethyl ester (3)

A sol. of compound 6 (49.8 g, 132 mmol) in THF (1.10 L) under nitrogen was cooled to −78° C. BuLi (1.6M in hexane, 88.0 mL, 143 mmol) was added. After 1 h, ZnCl$_2$ (1M in THF, 198 mL, 198 mmol) was added. The mixture was allowed to warm up to rt. Compound 2 (55.0 g, 112 mmol) in THF (100 mL) and then Pd(PPh$_3$)$_4$ (3.47 g, 3.00 mmol) were added. The mixture was heated to reflux for 1 h, and allowed to cool to rt. The mixture was diluted with EtOAc and washed with aq. 1M NaOH (1×). The org. extracts were dried over MgSO$_4$, filtered, and the solvents were removed under reduced pressure. Purification of the residue by FC (MeOH/CH$_2$Cl$_2$1:49→1:24→3:47→4:45) yielded the title product (47.3 g, 79%). LC-MS: $t_R$=0.95 min; ES+: 605.34.

2-(4-Bromophenoxy)ethanol (4)

To a sol. of 4-bromophenol (40 g, 231 mmol) in EtOH (140 mL) was added NaOH (10.2 g, 254 mmol). The resulting mixture was stirred at 70° C. for 30 min until the whole amount of NaOH had dissolved. A sol. of 2-bromoethanol (17.3 mL, 231 mmol) in EtOH (40 mL) was added dropwise at 70° C. The sol. rapidly turned milky. The mixture was heated to reflux overnight. The solvents were removed under reduced pressure, and the residue was dissolved in EtOAc. The mixture was washed with water and brine, dried over MgSO$_4$, filtered, and the solvents were removed under reduced pressure. Purification of the crude by FC (EtOAc/heptane 1:5→1:4→1:3→1:2→EtOAc) yielded the title compound (39.2 g, 78%) as a pale brown oil that crystallized when placed at −18° C. $R_f$=0.3 in (EtOAc/heptane 1:1).

1-Bromo-4-(2-iodoethoxy)benzene (5)

To a sol. of compound 4 (39.2 g, 181 mmol) in dry toluene (500 mL) was added imidazole (61.5 g, 903 mmol), PPh$_3$ (90 g, 343 mmol), and iodine (87.1 g, 343 mmol). This mixture was stirred at 60° C. for 2 h. The mixture was filtered over Celite, and the filtrate was concentrated under reduced pressure. Purification of the residue by FC (EtOAc/heptane 1:5→1:4→1:3→1:2→1:1) yielded the title compound (39.9 g, 67%).

Compound 6

In a 500-mL 3-necked flask equipped with a mechanical stirrer and a reflux condenser were mixed compound 5 (39.9 g, 122 mmol) and 2,6-dichloro-p-cresol (21.6 g, 122 mmol) in dry acetone (1200 mL). To this mixture was added K$_2$CO$_3$ (16.86 g, 122 mmol), and the resulting suspension was heated to reflux for 20 h. The reaction mixture was concentrated under reduced pressure, the residue was dissolved in EtOAc and this org. phase was washed with water (2×), and with brine (1×). The org. layer was dried over MgSO$_4$, filtered, and concentrated under reduced pressure. Purification of the residue by a short FC (EtOAc/heptane 1:9) yielded the title compound (44.4 g, 96%).

(rac.)-(1R*,5S*)-7-{4-[2-(2,6-Dichloro-4-methylphenoxy)ethoxy]phenyl}-3,9-diazabicyclo[3.3.1]non-6-ene-3,6,9-tricarboxylic acid 3,9-di-tert-butyl ester 6-ethyl ester (7)

Compound 3 (57.3 g, 94.6 mmol) was dissolved in dry 1,2-dichlorethane (1.00 L). NaHCO$_3$ (80.4 g, 946 mmol) and 1-chloroethyl chloroformate (103 mL, 946 mmol) were added, and the suspension was heated to 80° C. for 3 h. The reaction mixture was allowed to cool to rt. The mixture was filtered and the filtrate was evaporated under reduced pressure. The residue was dried for 15 min under high vacuum. The product was then diluted in MeOH (900 mL), and the mixture was heated to 60° C. for 30 min. The reaction mixture was allowed to cool to rt, and the solvents were removed under reduced pressure. The residue was dried under high vacuum for 1 h. The residue was dissolved in CH$_2$Cl$_2$ (1.00 L), and the sol. was cooled to 0° C. DIPEA (97.2 mL, 567 mmol), and Boc$_2$O (62.0 g, 283 mmol) were added. The reaction mixture was stirred at 0° C. for 30 min, then at rt for 30 min. The reaction mixture was diluted with CH$_2$Cl$_2$ (110 mL). The org. layer was washed with aq. 1M HCl (2×300 mL), and aq. sat. NaHCO$_3$ (300 mL). The org. layer was dried over MgSO$_4$, filtered, and the solvents were evaporated under reduced pressure. Purification of the residue by FC (EtOAc/heptane 1:5→1:38→1:1→EtOAc) yielded the title compound (47.9 g, 73%). LC-MS: $t_R$=1.22 min; ES+: 691.37.

Mixture of (rac.)-(1R*,5S*)-7-{4-[2-(2,6-dichloro-4-methylphenoxy)ethoxy]-phenyl}-3,9-diazabicyclo[3.3.1]non-6-ene-3,6,9-tricarboxylic acid 3,9-di-tert-butyl ester (8) and (rac.)-(1R*,5S*)-7-{4-[2-(2,6-dichloro-4-methylphenoxy)-ethoxy]phenyl}-3,9-diazabicyclo[3.3.1]non-7-ene-3,6,9-tricarboxylic acid 3,9-di-tert-butyl ester (9)

A mixture of compound 7 (47.8 g, 69.1 mmol) in aq. 1M NaOH (350 mL) and EtOH (700 mL) was stirred at 80° C. overnight. The mixture was partially evaporated under reduced pressure, and EtOAc (500 mL) was added. The aq. phase was acidified with aq. 3M HCl, and the mixture was extracted. The org. layer was separated, dried over $MgSO_4$, filtered, and the solvents were removed under reduced pressure. The residue was dried under high vacuum, giving a 1:1 mixture of compounds 8 and 9, which was used further without purification (50.2 g, quantitative yield). LC-MS: $t_R$=1.12 and 1.14 min; ES+: 663.33.

(rac.)-(1R*,5S*)-6-[Cyclopropyl-(2,3-dimethylbenzyl)carbamoyl]-7-{4-[2-(2,6-dichloro-4-methylphenoxy)ethoxy]phenyl}-3,9-diazabicyclo[3.3.1]non-6-ene-3,9-dicarboxylic acid di-tert-butyl ester (10)

A mixture of compounds 8 and 9 (14.6 g, 22.0 mmol), compound 11 (9.64 g, 55 mmol), EDC.HCl (12.7 g, 66.0 mmol), HOBt (3.72 g, 27.5 mmol), DMAP (672 mg, 5.50 mmol) and DIPEA (15.1 mL, 88 mmol) in $CH_2Cl_2$ (300 mL) was stirred at rt for 4 days. Twice were added EDC.HCl (2.10 g, 10.6 mmol) and compound 11 (3.85 g, 22.0 mmol). The mixture was diluted with more $CH_2Cl_2$, and was washed with aq. 1M HCl (3×), and aq. sat. $NaHCO_3$ (2×). The org. layer was dried over $MgSO_4$, filtered, and the solvents were removed under reduced pressure. Purification by FC yielded the title compound (13.8 g, 76%). LC-MS: $t_R$=1.20 min; ES+: 820.53.

Cyclopropyl-(2,3-dimethylbenzyl)amine (11)

A mixture of 2,3-dichlorobenzaldehyde (68.9 g, 514 mmol) and cyclopropylamine (72 mL, 1.02 mol) in dry MeOH (1300 mL) was stirred at rt overnight. The reaction mixture was cooled to 0° C., and $NaBH_4$ (25.3 g, 668 mmol) was added. The reaction mixture was stirred again at rt overnight. Ice was added to the reaction mixture, and the solvents were evaporated under reduced pressure. The residue was dissolved in EtOAc, and was washed with aq. 1M NaOH. The aq. layer was extracted with EtOAc (3×). The combined org. extracts were dried over $MgSO_4$, filtered, and the solvents were removed under reduced pressure. Purification of the residue by FC (EtOAc/heptane 9:1→1:1) yielded the title compound (78.4 g, 87%). LC-MS: $t_R$=0.84 min; ES+: 176.13.

Compound (I): (rac.)-(1R*,5S*)-7-{4-[2-(2,6-dichloro-4-methylphenoxy)-ethoxy]phenyl}-3,9-diazabicyclo[3.3.1]non-6-ene-6-carboxylic acid cyclopropyl-(2,3-dimethylbenzyl)amide A sol. of compound 10 (13.8 g, 16.9 mmol) in $CH_2Cl_2$ (120 mL) was cooled to 0° C. HCl (4M in dioxane, 120 mL) was added. The mixture was stirred for 1 h at 0° C., then 2 h at rt. The solvents were removed under reduced pressure, and the residue was dried under high vacuum. The residue was diluted with $CH_2Cl_2$, and washed with aq. 1M NaOH until the aq. layer staid basic. The org. extracts were dried over $MgSO_4$, filtered, and the solvents were removed under reduced pressure. Purification of the residue by FC (MeOH/$CH_2Cl_2$ 5:95→10:90→20:80 with 1% $Et_3N$ all the time) yielded the title compound (9.45 g, 90%). LC-MS: $t_R$=0.87 min; ES+: 620.40.

Compound (I'): (1R,5S)-7-{4-[2-(2,6-dichloro-4-methylphenoxy)ethoxy]-phenyl}-3,9-diazabicyclo[3.3.1]non-6-ene-6-carboxylic acid cyclopropyl-(2,3-dimethylbenzyl)amide Compound (I) (9.45 g, 15.2 mmol) was purified on a Regis Whelk 01 column, 50×250 mm using isocratic conditions (25% EtOH, 0.1% diethylamine, 75% hexane) and a flow of 100 mL/min. The desired compound came as first enantiomer ($t_R$=17.85 min). After evaporating the solvents under reduced pressure, the residue was dried under high vacuum. The residue was dissolved in $CH_2Cl_2$, and washed with aq. 10% $K_2CO_3$. The org. extracts were dried over $MgSO_4$, filtered, and the solvents were removed under reduced pressure. Drying the residue under high vacuum yielded the title compound (3.40 g).

Biological Assays

1. Enzyme Immuno Assay (EIA) to Estimate Ang I Accumulation and Renin Inhibition 1.1 Preparation of Ang I-BSA Conjugate 1.3 mg (1 µmol) of Ang I [1-10 (Bachem, H-1680)] and 17 mg (0.26 µmol) of BSA (Fluka, 05475) were dissolved in 4 mL of 0.1M phosphate buffer, pH 7.4, after which 2 mL of a 1:100 dilution of glutaraldehyde in $H_2O$ (Sigma G-5882) was added dropwise. The mixture was incubated overnight at 4° C., then dialyzed against 2 liters of 0.9% NaCl, twice for 4 h at rt, followed by dialysis against 2 liters of PBS 1× overnight at rt. The solution was then filtered with a Syringe filter, 0.45 µm (Nalgene, Cat. No. 194-2545). The conjugate can be stored in polypropylene tubes in 0.05% sodium azide at 4° C. for at least 12 months.

1.2 Preparation of BSA-Ang I Coated MTP

Microtiter plates (MPT384, MaxiSorp™, Nunc) were incubated overnight at 4° C. with 80 µl of Ang I (1-10)/BSA conjugate, diluted 1:100'000 in PBS 1× in a teflon beaker (exact dilution dependent on batch of conjugate), emptied, filled with 90 µl of blocking solution [0.5% BSA (Sigma A-2153) in PBS 1×, 0.02% $NaN_3$], and incubated for at least 2 h at rt, or overnight at 4° C. 96 well MTP (MaxiSorp™, Nunc) were coated with 200 µl conjugate and blocked with 250 µl blocking solution as above, except that the blocking solution contained 3% BSA. The plates can be stored in blocking solution at 4° C. for 1 month.

1.3 Ang I-EIA in 384 Well MTP

The Ang I (1-10)/BSA coated MTP were washed 3 times with wash buffer (PBS 1×, 0.01% Tween 20) and filled with 75 µl of primary antibody solution (anti-Ang I antiserum, pre-diluted 1:10 in horse serum), diluted to a final concentration of 1:100'000 in assay buffer (PBS 1×, 1 mM EDTA, 0.1% BSA, pH 7.4). 5 µl of the renin reaction (or standards in assay buffer) (see below) were added to the primary antibody solution and the plates were incubated overnight at 4° C. After the incubation the plates were washed 3 times with wash buffer and incubated with secondary antibody [anti-rabbit IgG, linked to horseradish peroxidase (Amersham Bioscience, NA 934V), diluted 1:2'000 in wash buffer] for 2 h at rt. The plates were washed 3 times with wash buffer and then incubated for 1 h at rt with substrate solution [1.89 mM ABTS (2.2'-azino-di-(3-ethyl-benzthiazolinsulfonate)] (Roche Diagnostics, 102 946) and 2.36 mM $H_2O_2$ [30%, (Fluka, 95300] in substrate buffer (0.1M sodium acetate, 0.05M sodium dihydrogen phosphate, pH 4.2). The OD of the plate was read at 405 nm in a microplate reader (FLUOStar Optima from BMG).

The production of Ang I during the renin reaction was quantified by comparing the OD of the sample with the OD of a standard curve of Ang I (1-10), measured in parallel.

2. Primary Renin Inhibition Assay: $IC_{50}$ in Buffer, 384 Well MTP

The renin assay was adapted from an assay described before (Fischli W. et al., *Hypertension*, 1991, 18:22-31) and consists of two steps: in the first step, recombinant human renin is incubated with its substrate (commercial human tetradecapeptide renin substrate) to create the product Angiotensin I (Ang I). In the second step, the accumulated Ang I is measured by an immunological assay (enzyme immuno assay, EIA). The detailed description of this assay is found below. The EIA is very sensitive and well suited for renin activity measurements in buffer or in plasma. Due to the low concentration of renin used in this assay (2 fmol per assay tube or 10 pM) it is possible to measure inhibitor affinities in this primary assay down to low pM concentration.

2.1 Methodology

Recombinant human renin (3 pg/μl) in assay buffer (PBS 1×, 1 mM EDTA, 0.1% BSA, pH 7.4), human tetradecapeptide (1-14) substrate (Bachem, M-1120) [5 μM in 10 mM HCl], hydroxyquinoline sulfate (Fluka, 55100) [30 mM in $H_2O$] and assay buffer were premixed at 4° C. at a ratio of 100:30:10:145. 47.5 μl per well of this premix was transferred into polypropylene plates (MTP384, Nunc). Test compounds were dissolved and diluted in 100% DMSO and 2.5 μl added to the premix, then incubated at 37° C. for 3 h. At the end of the incubation period, 5 μl of the renin reaction (or standards in assay buffer) were transferred into EIA assays (as described above) and Ang I produced by renin was quantified. The percentage of renin inhibition (Ang I decrease) was calculated for each concentration of compound and the concentration of renin inhibition was determined that inhibited the enzyme activity by 50% ($IC_{50}$).

The compound of formula (I') displays an $IC_{50}$-value of 0.3 nM.

Hemodynamic Measurements (Telemetry Method)

Animals—Female double transgenic rats with human renin and human angiotensinogen were purchased from RCC Ltd, Füllingsdorf, Switzerland. All animals were maintained under identical conditions and had free access to normal pelleted rat chow and water. Rats were initially treated with enalapril (1 mg/kg/day) during 2 months. After approximately two weeks following cessation of enalapril treatment the double transgenic rats become hypertensive and reach mean arterial blood pressures in the range of 160-170 mmHg.

Transmitter implantation—The rats were anaesthetised with a mixture of 90 mg/kg Ketamin-HCl (Ketavet, Parke-Davis, Berlin FRG) and 10 mg/kg xylazin (Rompun, Bayer, Leverkusen, FRG) i.p. The pressure transmitter was implanted under aseptic conditions into the peritoneal cavity with the sensing catheter placed in the descending aorta below the renal arteries pointing upstream. The transmitter was sutured to the abdominal musculature and the skin closed.

Telemetry-System—Telemetry units were obtained from Data Sciences (St. Paul, Minn.). The implanted sensor consisted of a fluid-filled catheter (0.7 mm diameter, 8 cm long; model TA11PA-C40) connected to a highly stable low-conductance strain-gauge pressure transducer, which measured the absolute arterial pressure relative to a vacuum, and a radio-frequency transmitter. The tip of the catheter was filled with a viscous gel that prevents blood reflux and was coated with an antithrombogenic film to inhibit thrombus formation. The implants (length=2.5 cm, diameter=1.2 cm) weighted 9 g and have a typical battery life of 6 months. A receiver platform (RPC-1, Data Sciences) connected the radio signal to digitized input that was sent to a dedicated personal computer (Compaq, deskpro). Arterial pressures were calibrated by using an input from an ambient-pressure reference (APR-1, Data Sciences). Systolic, mean and diastolic blood pressure was expressed in millimeter of mercury (mmHg).

Hemodynamic measurements—Double transgenic rats with implanted pressure transmitters were dosed by oral gavage with vehicle or 10 mg/kg of the test substance (n=6 per group) and the mean arterial blood pressure was continuously monitored. The effect of the test substance is expressed as maximal decrease of mean arterial pressure (MAP) in the treated group versus the control group.

The compound of formula (I') was active in this animal model. It led to a blood pressure decrease of 30 mmHg at a single oral dose of 10 mg/kg, and a blood pressure decrease of 17 mmHg at a single oral dose of 3 mg/kg.

The invention claimed is:

1. A compound of formula (I') named as (1R,5S)-7-{4-[2-(2,6-dichloro-4-methylphenoxy)ethoxy]phenyl}-3,9-diazabicyclo[3.3.1]non-6-ene-6-carboxylic acid cyclopropyl-(2,3-dimethylbenzyl)amide:

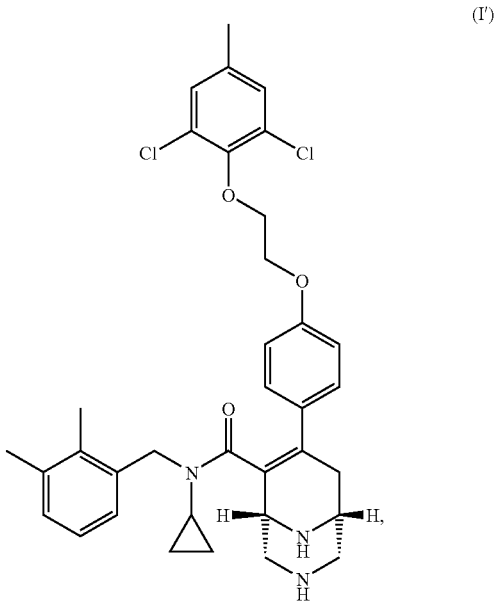

(I')

or a pharmaceutically acceptable salt thereof.

2. A pharmaceutical composition comprising the compound according to claim 1, or a pharmaceutically acceptable salt thereof, and a pharmaceutically acceptable carrier material.

* * * * *